(12) United States Patent
Alonso Chamarro et al.

(10) Patent No.: US 10,578,579 B2
(45) Date of Patent: Mar. 3, 2020

(54) PROBE FOR THE CONTINUOUS MONITORING IN REAL TIME OF CHEMICAL PARAMETERS OF INTEREST DIRECTLY IN THE GROUND AND SYSTEM FOR THE CONTINUOUS MONITORING IN REAL TIME OF SAID CHEMICAL PARAMETERS OF INTEREST

(71) Applicant: Universitat Autonoma de Barcelona, Bellaterra Barcelona (ES)

(72) Inventors: Julian Alonso Chamarro, Bellaterra Barcelona (ES); Eva Arasa Puig, Bellaterra Barcelona (ES)

(73) Assignee: Universitat Autonoma de Barcelona (ES)

( * ) Notice: Subject to any disclaimer, the term of this patent is extended or adjusted under 35 U.S.C. 154(b) by 0 days.

(21) Appl. No.: 15/531,251

(22) PCT Filed: Nov. 25, 2015

(86) PCT No.: PCT/ES2015/070853
§ 371 (c)(1),
(2) Date: May 26, 2017

(87) PCT Pub. No.: WO2016/083649
PCT Pub. Date: Jun. 2, 2016

(65) Prior Publication Data
US 2017/0322179 A1 Nov. 9, 2017

(30) Foreign Application Priority Data
Nov. 26, 2014 (ES) .................................. 201431756

(51) Int. Cl.
*G01N 27/416* (2006.01)
*G01N 33/24* (2006.01)
*G01N 27/403* (2006.01)

(52) U.S. Cl.
CPC ..... *G01N 27/4161* (2013.01); *G01N 27/4035* (2013.01); *G01N 33/24* (2013.01); *G01N 2033/245* (2013.01)

(58) Field of Classification Search
CPC ........... G01N 27/4161; G01N 27/4035; G01N 33/24; G01N 2033/245
See application file for complete search history.

(56) References Cited

U.S. PATENT DOCUMENTS 3,847,351 A    11/1974    Hasenbeck
4,288,357 A    9/1981    Kanazawa et al.
(Continued)

FOREIGN PATENT DOCUMENTS

DE    19714474 A1    10/1998
DE    19842735 A1    3/2000
(Continued)

OTHER PUBLICATIONS

Machine translation to English for WO 2011/127905 A1 (Year: 2011).*
(Continued)

*Primary Examiner* — J. Christopher Ball
(74) *Attorney, Agent, or Firm* — Hayes Soloway PC

(57) ABSTRACT

The monitoring probe (1) comprises: a FR-4 substrate (2) with two faces; two copper tracks (3) arranged on one of the faces of the substrate (2), with an electrical contact terminal (7) on the outside of the probe (1); a conductive region (6) with reference electrode functions, with an electrical contact terminal (8) on the outside of the probe (1), occupying the entire other face of the substrate (2); a passivating material layer (5) partially covering the copper tracks (3) and leaving two free zones (12, 13) of said tracks (3) uncovered, one of said free zones (12) corresponding to the electrical contact terminal (7) of the two copper tracks (3); and two ISE sensor
(Continued)

elements (4) that are sensitive to at least one of the parameters of interest to be monitored in the ground, and arranged in the other of the free zones (13) of the two copper tracks (3).

15 Claims, 9 Drawing Sheets

(56) References Cited

U.S. PATENT DOCUMENTS

| | | |
|---|---|---|
| 6,800,158 B2 | 10/2004 | Polikarpus et al. |
| 2001/0008691 A1 | 7/2001 | Isogai et al. |
| 2003/0209451 A1 | 11/2003 | Dineen et al. |
| 2008/0149501 A1 | 6/2008 | Heule et al. |
| 2010/0051457 A1 | 3/2010 | Hsiao et al. |

FOREIGN PATENT DOCUMENTS

| | | |
|---|---|---|
| DE | 10022210 A1 | 11/2001 |
| DE | 102006021432 A1 | 12/2006 |
| DE | 102006025098 A1 | 11/2007 |
| EP | 0302228 A2 | 2/1989 |
| EP | 1347058 A2 | 9/2003 |
| JP | H03162660 A | 7/1997 |
| WO | 0165247 A1 | 9/2001 |
| WO | 2009157755 A3 | 12/2009 |
| WO | 2011034413 A1 | 3/2011 |
| WO | 2011127905 A1 | 10/2011 |
| WO | 2012115501 A1 | 8/2012 |
| WO | 2014176179 A2 | 10/2014 |

OTHER PUBLICATIONS

Ibanez-Garcia, et al. "Biparametric Potentiometric Analytical Microsystem Based on the Green Tape Technology", Electroanalysis, 22(20): p. 2376-2382, Jul. (Year: 2010).*

Machine Translation to English of DE 10201001551 A1 (Year: 2010).*

Martinez-Cisneros et al.,"Wireless sensor network based on green tape technology for in-soil nutrients monitoring", Ibersensor, Oct. 2012, pp. 16-19, Puerto Rico.

* cited by examiner

PROBE FOR THE CONTINUOUS MONITORING IN REAL TIME OF CHEMICAL PARAMETERS OF INTEREST DIRECTLY IN THE GROUND AND SYSTEM FOR THE CONTINUOUS MONITORING IN REAL TIME OF SAID CHEMICAL PARAMETERS OF INTEREST

TECHNICAL FIELD OF THE INVENTION

The present invention is comprised within the technical field of monitoring and measuring parameters of interest in the ground and particularly in agricultural crops.

More specifically, the invention is aimed at a probe for continuously obtaining in situ analytical information on soil composition in real time, i.e. directly in the ground or agricultural crop, and to a system for obtaining said information by means of said probe.

STATE OF THE ART

The correct use of resources such as water and fertilisers in agriculture, which is the main source of livelihood of the world's population, is of great importance both from an economic (optimisation of production processes) and environmental (reduction of the negative impact of intensive cultivation) standpoint. The ability to rationalise the use of these resources by applying concepts of so-called precision farming requires obtaining useful information that indicates the state of the environment and the changes that occur therein in the shortest possible time, thereby giving rise to what is currently known as smartfields.

For farmers, the systematic recording of information helps them to implement quality systems with the aim of standardising the management of production processes, improving the flow of information and decision-making to reduce losses or inefficiencies. Additionally, knowing the historical and current state of the environment makes it possible to ascertain the need for fertigation, thereby minimising production costs.

For society, the optimisation of resources in agriculture is also of vital importance, since not only does it consume most of the available water resources, but also contaminates the water, particularly underground water, causing an unsustainable environmental impact.

Traditionally, analytical information has been obtained by means of grab sampling in accessible zones. Subsequently, the samples are transported to a laboratory equipped for the measuring thereof. This involves longer analysis times and obtainment of results in a discontinuous manner. The main limitations of this classical approach are the need for sampling, preserving and transporting the samples, which dramatically increases the economic cost and only provides discreet information both from a temporal and spatial viewpoint. At the same time, in order to monitor the different parameters it is essential to use sophisticated instrumentation characterised in that it has a high acquisition cost and in that it has a permanent need for qualified personnel. All these factors cause the procedures to be slow, significantly delaying the obtainment of information, in addition to being very expensive.

Thus, from a practical viewpoint and in order to satisfy customer needs, new analytical strategies capable of providing information quickly and continuously, for example by simplifying the information the customer needs for that specific analytical problem, in an understandable manner, at an affordable cost and correlatable with the information that would be obtained using the above-referenced method are required.

In the field of monitoring parameters in agricultural crops, it is of great importance to obtain continuous and real-time information in situ, i.e. in the ground. Knowing the state of the environment, the changes generated therein together with historical information between different harvests, helps to ascertain the real needs of the crop without squandering resources. That is, in order to cover this great demand for information, the development of new, robust, portable and affordable instruments is required.

The most significant costs in an agricultural holding are those related to irrigation and fertilisation, the latter being the highest. To date, fields are fertilised regularly without knowing if it is really necessary. Thus, there is a tendency to overfertilise, with the ensuing costs. Additionally, this not only represents a surcharge on production but also entails an adverse environmental impact. In recent years, the overfertilisation of fields together with the indiscriminate pouring of pig slurry has led to the contamination of underground aquifers, particularly by nitrates, rendering them useless as sources of water for human consumption.

Therefore, access to continuous and historical information on the concentration (patterns) of different analytes of interest in the soil would make it possible to improve production processes and minimise the environmental problems derived therefrom. Ideally, the information required is that concerning ground water concentration/patterns. Additionally, knowing these concentrations/patterns at different soil depths could help to understand the processes responsible for mobilising these species through the soil profile in accordance with factors such as its composition, the existence of roots, humidity, temperature, etc.

In the context of the present invention, reference will be made interchangeably to the soil or ground to be monitored. Potential instrument devices for environmental monitoring are chemical sensors. They have the advantage of being capable of providing real-time information and their miniaturisation and implementation in battery-fed portable equipment is also possible, due to which they can be used outside the laboratory.

A chemical sensor can be defined as a robust, portable, user-friendly device that provides continuous information about the concentration of the analyte of interest in the environment. Two parts can be distinguished: the recognition element, which selectively interacts with the sample analyte, and the transducer that transforms the response into a measurable signal which is normally electrical. These parts can be physically separated or integrated in the transducer as such. The information transmitted will be of the quantitative type, since its magnitude will be related to the concentration (or activity) of the species of interest.

Chemical sensors, in addition to providing a quick response, being inexpensive and sufficiently selective, are also capable of dramatically simplifying the stages of the analytical process, reducing them to analyte recognition and transduction of the signal generated by this recognition.

There are various types of chemical sensors (electrical, optical, mass and thermal). Among these, electrochemical sensors are especially attractive due to their instrumental and operational simplicity, and their low cost. Additionally, they have already reached a commercial stage and can be used for a large number of applications in the clinical, industrial, environmental and agricultural field.

Among electrochemical sensors we can distinguish voltamperometric, conductometric and potentiometric sensors, the latter being the most interesting.

The theoretical expression that quantitatively relates signal and activity/concentration in the potentiometric technique is the Nernst equation (Eq. 1). The theoretical sensitivity for monovalent ions is 59.16 my/decade of concentration at 25° C.

$$E_M - k + \frac{R \cdot T}{z_i \cdot F} \cdot \log[a_i] \qquad \text{(Eq. 1)}$$

where $E_M$ is the potential supplied by the indicator electrode, k is a constant, R is the gas constant (8.314 J/K·mol), T is temperature, F is the Faraday constant ($9.6487 \cdot 10^4$ C·mol$^{-1}$), $z_i$, and $a_i$ are the charge and activity of the main ion (or analyte), respectively.

In the potentiometric sensors, the signal measured, using a high-impedance voltmeter, corresponds to the potential difference between the indicator electrode and the reference electrode. That is, the reference electrode represents half of the cell and has the same operational importance as the indicator electrode.

The ion-selective electrodes (ISE) are a type of potentiometric sensor and are constituted by membranes characterised in that they generate an electrical membrane potential in accordance with the activity/concentration of a certain species existing in the medium in contact therewith. However, they can also modify the potential generated in the presence of other species (interferents) although to a lesser extent, i.e. the signals generated by the membrane are selective but not specific.

Potentiometric sensors are characterised in that they provide information about the activity or concentration of species in ionic form and not of the total content of these species. This fact is of great importance, since the information provided by these devices is directly related to the bioaccessible forms of nitrogen, phosphorus, carbon, etc. Thus, monitoring ions such as nitrate, potassium, calcium, chloride, phosphate or bicarbonate in the soil makes it possible to know the concentration of the species that are actually available for consumption by the roots of the crop. On the contrary, the reference techniques currently used provide information on the total content, which does not provide the information actually required.

These sensors are also used to determine the parameters of interest in dissolutions obtained by direct or sequential extraction of discreet samples taken from the soil, but the process is very painstaking and entails high labour costs. The concentration measured under these conditions depends, in any case, on the extractant solution used and alters the real conditions of absorption of nutrients by the crops.

The present invention solves the foregoing problems by means of a probe and monitoring system that makes it possible to quickly obtain continuous and historical information on the concentration (patterns) of different analytes of interest in the soil and, in particular, information on the concentration of the species that are really available for consumption by the roots of a crop, thereby making it possible to improve the production processes and minimising the environmental problems derived from the excessive use of fertilisation.

Likewise, the probe and system of the invention make up a robust, portable and affordable analytical instrumentation.

SUMMARY OF THE INVENTION

The use of so-called "nutrition probes" is proposed for the continuous monitoring of analytes or parameters of interest directly in the ground. These probes must function properly outdoors, fully or partially buried in the soil. Therefore, the probe must be designed so that electricity-sensitive zones are completely insulated from humidity, derived not only from ambient humidity but also from crop irrigation. Additionally, in order to ensure the medium- and long-term proper functioning of the nutrition probe, the impact of the bacterial and microbiological fauna inherent in the soil on the response/operability of the probe must also be taken into account.

Likewise, given the complexity and variability of the composition of the soils, in addition to the harshness of the ambient conditions in which the continuous in situ measurements are made with the probes, the levels of accuracy and precision obtained cannot be the same as those required under controlled laboratory conditions. Thus, it can be considered that field measurements provide continuous real-time information on the evolution of the concentration of the species of interest in the soil and, therefore, the probe of the invention must be considered a diagnostic or screening device. This information shows the variation of said concentration by leaching through the soil profile or by absorption by the crop with a level of precision comparable to that of other analytical systems of environmental application designed to acquire real-time information in situ. This semi-quantitative information makes it possible to adopt the necessary corrective measures in real time in terms of fertigation, in order to optimise production costs and limit the adverse environmental impact.

The invention provides a solution to the problems mentioned in the preceding section by means of a probe for the continuous monitoring in real time of parameters of interest directly in the ground, according to claim 1, a system for continuous monitoring in real time, according to claim 8, and a method for the continuous monitoring in real time of parameters of interest directly in the ground, according to claim 12. Preferred embodiments of the invention are defined in the dependent claims.

Thus, in a first inventive aspect, the invention presents a probe for the continuous monitoring in real time of parameters of interest directly in the ground comprising:

a substrate with at least two faces, at least one conductive material track arranged on at least one of the at least two faces of the substrate, with a zone adapted to act as an electrical contact terminal on the outside of the probe, a conductive region with reference electrode functions, with a zone adapted to act as an electrical contact terminal outside of the probe, at least one passivating material layer arranged such that it partially covers the at least one conductive material track and leaves at least two free zones thereof uncovered, one of said free zones corresponding to the electrical contact terminal of the at least one conductive material track, and at least one sensor element sensitive to at least one of the parameters of interest to be monitored in the ground, deposited in at least one of the free zones of the at least one conductive material track.

This probe enables the continuous monitoring of parameters or analytes of interest (nitrate, potassium, calcium, chloride, phosphate, bicarbonate, etc.) directly in soils in an inexpensive and simple manner. The probe makes it possible to measure a wide variety of parameters of interest by simply selecting the adequate sensor element, i.e. sensitive to the parameter of interest to be measured, and functions properly outdoors, fully or partially buried in the soil.

In the context of the invention, the at least one conductive material track can be made of any conductive metal or polymer composite or, in general, of any conductive substance on which the at least one sensor element can be deposited and adequately adhered. In one embodiment the at least one conductive material track is a metal sheet, specifically a flexible sheet composed by a (laminated) wrought copper and electrodeposited sheet.

The zone where the sensor element or membrane is deposited can be identified in the present invention as a transducer or internal conductive support of the sensor element or membrane. Said zone is a segment of the conductive material track not coated by the layer of passivating material.

The substrate can be made from a wide range of materials, both rigid and flexible. Substrate materials include, inter alia, the following:

Rigid materials: laminated materials such as BT-epoxy, compound epoxy materials, CEM-1.5, Cyanate ester, FR-2 or FR-4.

Flexible materials: polyester (PET), polyimide (PI), polyethylene naphthalate (PEN), polyetherimide (PEI), together with various fluoropolymers (FEP) and polyimide film copolymers.

In a particular embodiment, the probe for the continuous monitoring in real time of parameters of interest directly in the ground, the FR4 substrate, the at least one conductive region with reference electrode functions has biocidal properties and the at least one sensor element is an ion-selective electrode (ISE). Preferably, the conductive material track and the conductive region with reference electrode functions are made of copper.

In another embodiment, the at least one conductive material track and the at least one conductive region with reference electrode functions are metallic, such as copper, silver, gold, etc.; or non-metallic, such as for example inks and graphite composites, conductive polymers or conductive nanomaterials, such as for example metallic nanoparticles, carbon nanotubes or graphene.

FR4 is an affordable and mass produced material consisting of sheets of a material composed of fibreglass fabric woven with an epoxy resin binder. This material is characterised in that it is flame-resistant and in that it has a water absorption percentage of less than 0.1%. Additionally, it is capable of retaining the electrical insulation qualities both in dry and humid conditions. The at least one conductive material track is arranged on the FR4.

The machining of the FR4 substrate, i.e. the definition of its conductive structures, can be carried out by means of laser ablation or by chemical attack.

Advantageously, the selection of this substrate material provides a structurally resistant probe for use in the field and functions properly outdoors, fully or partially buried in the ground, given its low water absorption coefficient and its good electrical insulation qualities in humid conditions.

The conductive region that acts as a reference electrode has biocidal properties, i.e. it acts as a bactericide, preventing the bacteria in the ground from degrading sensitive parts of the probe such as sensor elements, a fact of great importance for the proper functioning of the probe in the short and long term.

The at least one conductive region that acts as a reference electrode is arranged on one of the faces, on some of them or on all of them. In one embodiment, the at least one conductive region preferably occupies one of the faces of the substrate in its entirety. Advantageously, this enables enhanced functioning as a reference electrode, which is of great importance for the functioning of the probe.

In one embodiment of the invention, the probe for the continuous monitoring in real time of parameters of interest directly in the field comprises two ISE sensor elements.

Advantageously, this embodiment provides greater versatility in the sense that each sensor element can be sensitive thereto or to different parameters of interest.

In another embodiment of the invention, the monitoring probe comprises more than one sensor element, arranged at the same height with respect to the dimensional configuration of the probe. Advantageously, this embodiment provides greater versatility in the sense that each sensor element may be sensitive thereto or to different parameters of interest. Advantageously, in the event that less than two of the sensor elements are sensitive to the same parameter of interest, the embodiment allows for a larger number of measurements and, therefore, a higher degree of precision of the parameter of interest measured in the work area of the sensor elements.

In yet another embodiment of the invention, the monitoring probe comprises more than one sensor element and these are arranged at different heights.

Advantageously, this embodiment enables monitoring at different ground depths.

In another embodiment of the invention, the monitoring probe comprises more than one sensor element and each sensor element is sensitive to a single soil parameter of interest.

Advantageously, this embodiment enables a larger number of measurements and, therefore, a higher degree of precision of the parameter of interest measured in the work area of the sensor elements.

In another embodiment of the invention, the monitoring probe comprises more than one sensor element and each sensor element is sensitive to a different soil parameter of interest.

Advantageously, this embodiment provides greater versatility to the monitoring probe, since information on different parameters of interest can be obtained with the same probe.

Lastly, in still another embodiment of the invention, the monitoring probe comprises a receptacle adapted to house a portion of soil of the ground to be monitored, near the at least one sensor element of the monitoring probe.

This embodiment makes it possible to maintain the portion of soil that houses the receptacle near the at least one sensor element. Thus, the portion of soil in contact with the membrane cannot be washed away by fertigation or rain water.

Additionally, the receptacle comprises a liquid-porous zone in a substantially lower zone thereof for enabling the evacuation of rain or fertigation water.

In a second aspect of the invention, a system for the continuous monitoring in real time of parameters of interest directly in the ground is provided comprising, at least one probe for the continuous monitoring in real time of parameters of interest directly in the ground according to a first inventive aspect, and at least one electronic circuit connected to the monitoring probe for the acquisition and adaptation of at least two electrical signals generated by said monitoring probe.

Advantageously, this second aspect of the invention enables the continuous monitoring of parameters or analytes of interest (nitrate, potassium, calcium, chloride, phosphate, bicarbonate, etc.) directly in the ground, by means of the acquisition and adaptation of at least two electrical signals generated by the probe in an inexpensive, versatile and simple manner.

In one embodiment of the system for the continuous monitoring in real time of parameters of interest directly in the ground, the connection of the at least one electronic circuit to the at least one probe is electrical and is performed through the probe contact terminals.

Advantageously, this embodiment enables the rapid, inexpensive and simple connection of the monitoring probe to the electronic circuit for the acquisition and adaptation of the two electrical signals generated by said monitoring probe.

In one embodiment of the monitoring system the connection of the at least one electronic circuit to the at least one probe is through a wireless connection (e.g.: XBee, ZBee, Bluetooth, Wi-Fi, RFID, etc.).

Advantageously, this embodiment enables a simpler and more affordable connection between the probe and the electronic circuit for the acquisition and adaptation of the two electrical signals generated by said monitoring probe, without the need to establish a cable connection between the two elements.

In another embodiment of the invention, the monitoring system comprises a datalogger connected to the electronic circuit for the acquisition and adaptation of the electrical signals generated by the monitoring probe. Alternatively, data is recorded using a datalogger such as a computer, in which all the information from the electronic circuit for the acquisition and adaptation of the electrical signals generated by the monitoring probe is stored. Similarly, both the datalogger and the computer are adapted to receive signals from different sequential probes or simultaneously. The advantage of these embodiments is that they enable the possibility of locally recording all the data of measurements made by the probe, in addition to the possibility of accessing said data from any device connected to the Internet.

In one embodiment, the connection of at least one electronic circuit for the acquisition and adaptation of the electrical signals to the datalogger is through cable or wireless (e.g.: XBee, ZBee, Bluetooth, Wi-Fi, RFID, etc.).

The cable connection enables a fast, inexpensive and simple connection of the electronic circuit for the acquisition and adaptation of the electrical signals to the datalogger.

Furthermore, the wireless connection enables a simpler and cheaper connection between the electronic circuit for the acquisition and adaptation of the two electrical signals generated by said monitoring probe and the datalogger, without the need to establish a cable connection between the two elements.

In another embodiment, the electronic circuit for the acquisition and adaptation of the at least two electrical signals generated by the monitoring probe is physically comprised within the probe itself.

In a third aspect of the invention, a method is provided for the continuous monitoring in real time of parameters of interest directly in the ground, characterised in that it comprises the following stages:
 a. Providing a monitoring system according to the second inventive aspect,
 b. Installing the probe in the ground to be monitored, and
 c. Collecting the data from the ground being monitored by means of the datalogger or a local data storage system.

Advantageously, this third aspect of the invention enables the continuous monitoring of the parameters or analytes of interest (nitrate, potassium, calcium, chloride, phosphate, bicarbonate, etc.) directly in the ground, by means of the acquisition and adaptation of at least two electrical signals generated by the probe in an inexpensive, versatile and simple manner, locally recording all the data from measurements made by the monitoring probe.

In one embodiment of the method for the continuous monitoring of parameters of interest directly in the ground, the installation of the probe in the ground to be monitored comprises the following stages:
 Making a hole in the ground sufficiently large to house the probe and with a depth dependent on the profile of the ground in which the parameters of interest will be monitored,
 Obtaining a viscous sludge by mixing a sieved fraction of the ground to be monitored with water,
 Introducing the probe in the hole made in the ground,
 Filling the hole with the probe filled with the viscous sludge, and
 Covering the zone of the hole with the probe filled with the viscous sludge with a portion of soil of the ground itself.

In another embodiment of the invention, the sieved fraction of the ground to be monitored has a particle size preferably comprised between 15 and 200 microns.

Advantageously, this particle size range ensures that the contact between the ground water and the sensor element, or membrane, is adequate. Larger-sized particles could cause a reduction in the zone of the sensor element exposed to the solution.

All the characteristics and/or stages of methods described in this specification (including the claims, description and drawings) may be combined in any combination, except mutually excluding combinations of such characteristics.

DESCRIPTION OF THE FIGURES

As a complement to the description being made, and for the purpose of helping to make the characteristics of the invention more readily understandable, in accordance with a preferred example of a practical embodiment thereof, said description is accompanied by a set of drawings constituting an integral part thereof which, by way of illustration and not limitation, represent the following.

DETAILED DESCRIPTION OF THE INVENTION

Figure 1A:
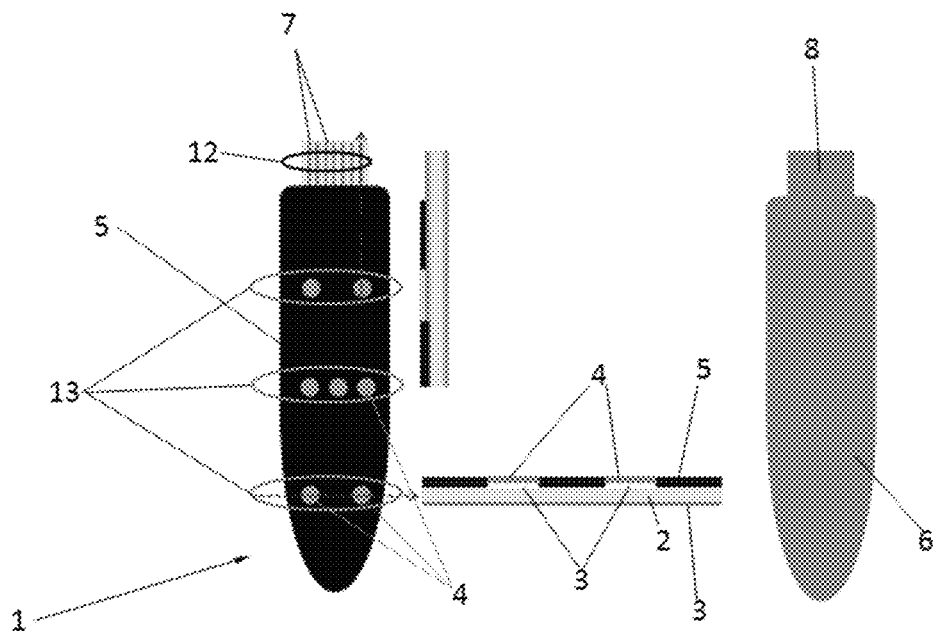
FIG. 1A shows an example of a monitoring probe of the invention with a detailed cross-section thereof.

The monitoring probe (1) according to the invention, as can be observed in the embodiment of FIG. 1, comprises a substrate (2) with two faces, a plurality of conductive material tracks (3) arranged on one of the two faces of the substrate (2), with a zone adapted to act as an electrical contact terminal (7) outside of the probe (1) and a conductive region (6) with reference electrode functions, with a zone adapted to act as an electrical contact terminal (8) outside of the probe (1).

Likewise, the probe comprises a passivating material layer (5) arranged in such a manner as to partially cover the plurality of conductive material tracks (3) and leaves at least two free zones (12, 13) of said conductive material tracks (3) uncovered, one of said free zones (12) corresponding to the electrical contact terminal (7) of the plurality of conductive material tracks (3).

The probe also comprises a plurality of sensor elements (4) sensitive to at least one of the parameters of interest to be monitored in the ground, deposited in the other of the free zones (13) of the plurality of conductive material tracks (3).

In a particular embodiment, the substrate (2) is FR4, the plurality of conductive tracks (3) and the conductive region (6) with reference electrode functions are made of copper, and the sensor element (4) is an ion-selective electrode or ISE.

In another embodiment, the conductive region (6) with reference electrode functions occupies the other face of the substrate (2) in its entirety.

In these embodiments, each of the sensor elements (4) requires a conductive track (3) in order to extract the signal, together with the signal that will similarly be extracted from the conductive region (6) towards the corresponding electronic circuit (9) for the acquisition and adaptation of the two electrical signals generated by said monitoring probe (1).

In these embodiments, the copper of the conductive region (6) fulfils various functions. The first function of this region is that of acting as a reference electrode (Cu/CuO), this being as important in the functioning of the sensor as the ISE sensor itself.

The second function fulfilled by the copper of the conductive region (6) is the biocidal or bactericidal function, preventing bacteria in the ground from degrading the sensitive parts of the probe, such as the membranes of the ISE sensor elements, which is of great importance to the proper functioning of the monitoring probe (1) in the short and long term.

Lastly, the third and final function of this conductive region (6) is that of acting as earth/mass for the monitoring system, shielding the signals supplied by the probe (1) and generating signals minimally affected by the electrical noise.

In one exemplary embodiment, the conductive tracks (3) comprise at least two layers of conductive material successively deposited on the substrate (2).

Furthermore, the probe (1) for the continuous monitoring in real time of parameters of interest directly in the ground according to any of the foregoing embodiments is connected to an electronic circuit (9) for the acquisition and adaptation of the two electrical signals generated by said monitoring probe (1), making up the system for the continuous monitoring in real time of parameters of interest directly in the ground.

The electronic circuit (9) is electrically connected to the probe (1) through the contact terminals (7, 8) of the probe (1).

In another embodiment, the system for the continuous monitoring in real time of parameters of interest directly in the ground additionally comprises a datalogger (10) connected to the electronic circuit (9) for the acquisition and adaptation of the electrical signals generated by the monitoring probe (1).

FIGS. 2A to 2E show different embodiments for transmitting data from the monitoring probe (1) to the data acquisition circuit (9) and/or the datalogger device (10) or computer for storing the data.

Figure 2:
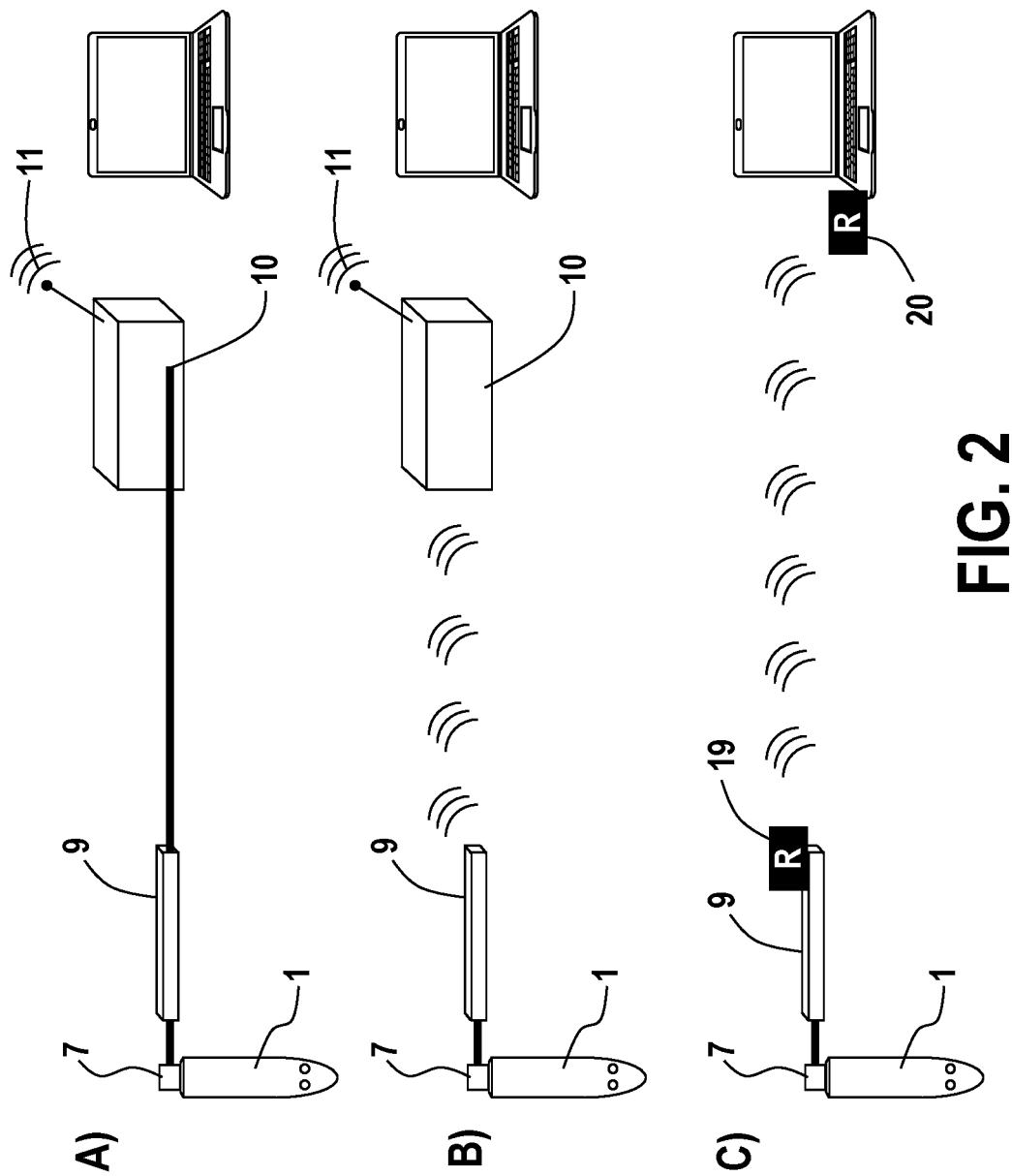
FIG. 2 shows block diagrams of different configurations for communicating the data of the monitoring probe of the invention to the data acquisition circuit and/or the datalogger.
Figure 2:
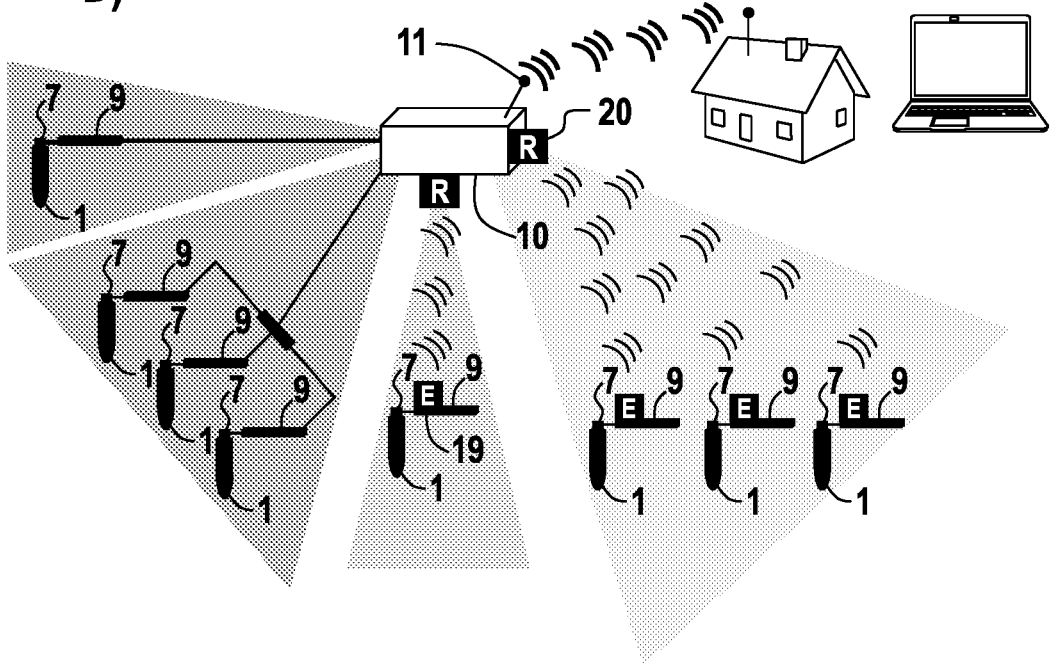
Figure 2:
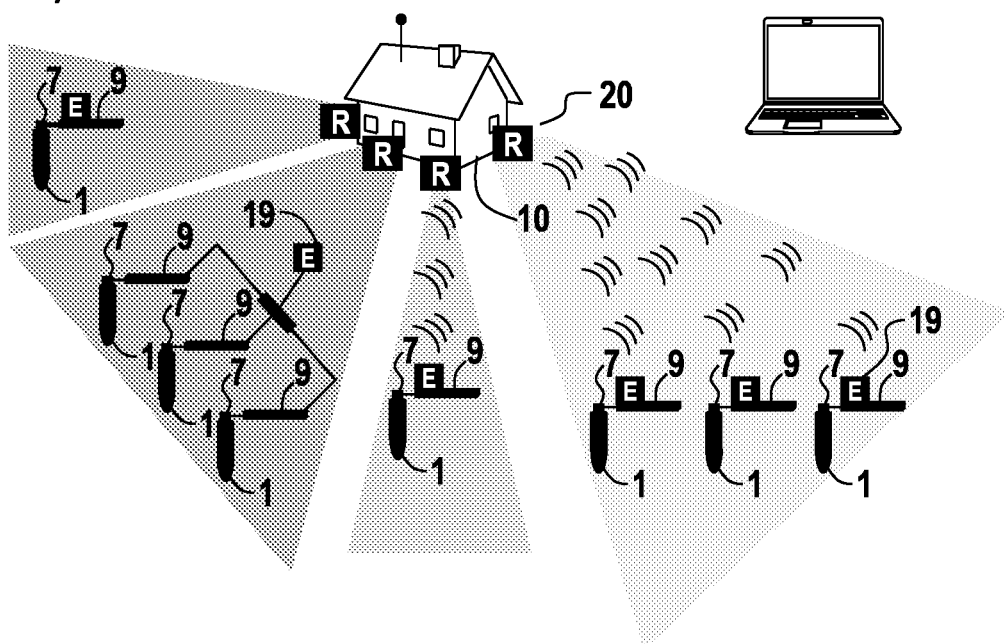
Figure 3:
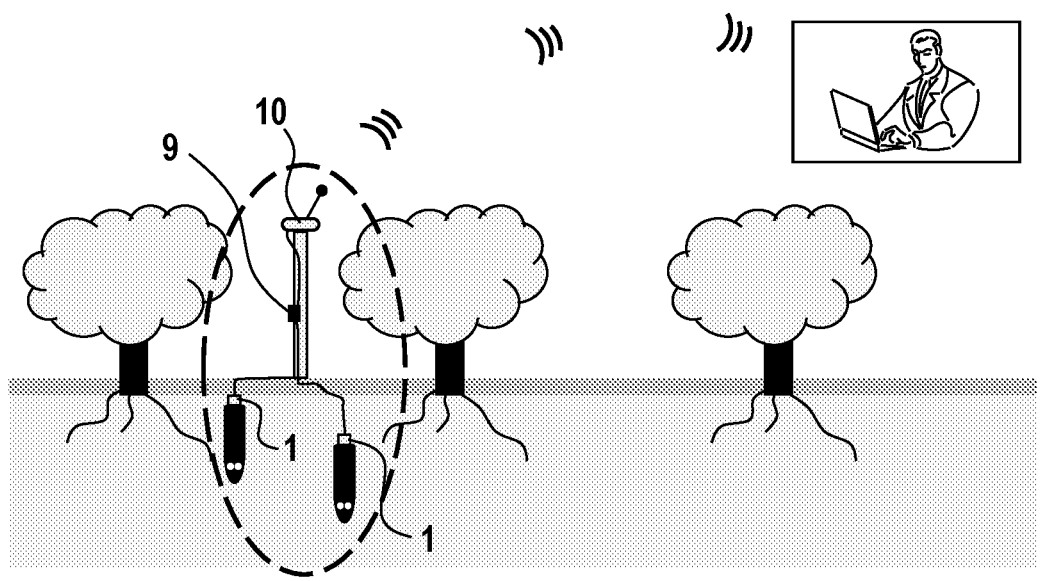
FIG. 3 shows a schematic view of the monitoring system of the invention with remote transmission of the information obtained.

FIG. 2 A) shows an embodiment wherein the monitoring probe (1) is connected by cable to the data acquisition device (9), and this in turn to the datalogger (10) also by cable. In turn, the datalogger (10) has a communications module (11) for transmitting the recorded data, preferably wirelessly, to a computer or local data storage system.

FIG. 2 B) shows an alternative embodiment wherein the data acquisition circuit (9) and datalogger (10) are wirelessly connected.

FIG. 2 C) shows an embodiment wherein the data acquisition circuit (9) has an emitter (19) for direct wireless communication, i.e. without the intervention of a datalogger, and wireless with a data receiver, such as a PC-type computer, having a receiver (20) for such purpose.

FIG. 2 D) shows an embodiment with a plurality of monitoring probes (1) wherein some of the probes (1) are connected by cable to a data acquisition circuit (9) and these in turn to a datalogger (10) also by cable or wirelessly. In turn, the datalogger (10) has a communications module (11) for transmitting the recorded data, preferably wirelessly.

FIG. 2 E) shows an embodiment also having a plurality of monitoring probes (1), wherein the probes (1) are connected by cable to a data acquisition circuit (9) and these in turn directly and wirelessly to a data-receiving device, such as a PC-type computer. To this end, each data acquisition circuit (9) has an emitter (19) and the data-receiving device has a receiver (20).

Figure 1B:
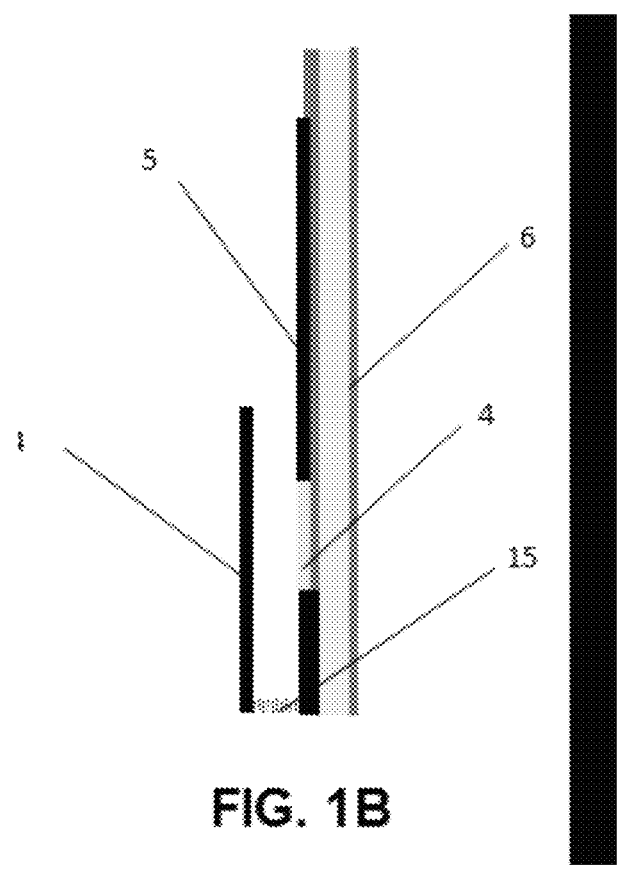
FIG. 1B shows an example of a monitoring probe of the invention comprising a receptacle adapted to house a portion of soil of the ground to be monitored near the at least one sensor element.

Lastly, in another embodiment of the invention, as can be observed in FIG. 1B, the monitoring probe comprises a receptacle (14) adapted to house a portion of soil of the ground to be monitored, near the sensor element (4) of the monitoring probe (1). This embodiment makes it possible to maintain the portion of soil that houses the receptacle near the at least one sensor element, ensuring the stability of the measurement zone by preventing the loss of the sensor element-soil contact in the event that the sensor is washed away during the fertigation process or by rainwater.

Likewise, said receptacle (14) may comprise a liquid-porous zone (15) in a substantially lower zone thereof to allow the evacuation of rain or fertigation water.

Assay with monitoring probes (measurement of Nitrate and Potassium)—Preparation.

Figure 4:
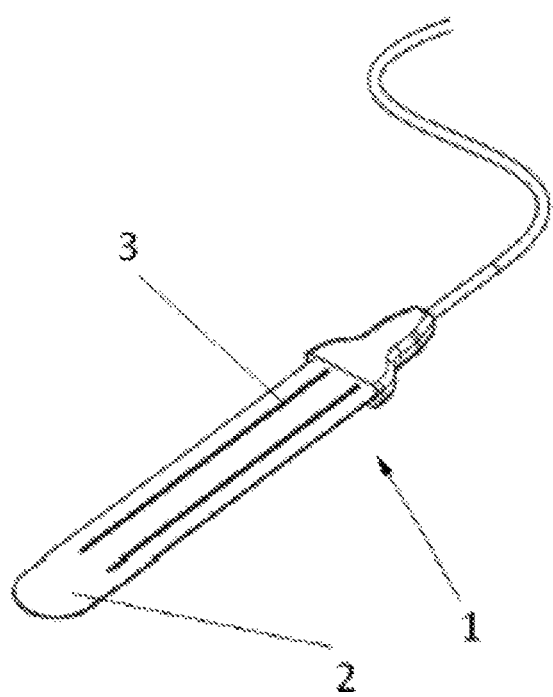
FIG. 4 shows an exemplary embodiment of the monitoring probe of the invention wherein two conductive material tracks without a sensor element can be observed.

In the exemplary embodiment shown in FIG. 4, the monitoring probe (1) comprises a substrate (2) of FR4 with two faces, two copper tracks (3) arranged on one of the two faces of the substrate (2), with a zone adapted to act as an electrical contact terminal (7) outside of the probe (1), and a conductive region (6) with reference electrode functions, with a zone adapted to act as an electrical contact terminal (8) on the outside of the probe (1), occupying the entire other face of the substrate (2).

Likewise, in this exemplary embodiment the probe comprises a passivating material layer (5) arranged such that it partially covers the two copper tracks (3) and leaves two free zones (12, 13) of the two copper tracks (3) uncovered, one of said free zones (12) corresponding to the electrical contact terminal (7) of the two copper tracks (3); and two ISE sensor elements (4) sensitive to at least one of the parameters of interest to be monitored in the ground, deposited on the other of the free zones (13) of the two copper tracks (3).

At the end of the probe (1), specifically in the contact terminals (7, 8), the electrical cables that connect each of the ISE sensor elements (4) of the probe (1) to conductive region (6), which acts as a Reference electrode, were welded to the electronic circuit (9) for the acquisition and adaptation of the electrical signals.

In this assay, the potassium- and nitrate-sensitive ISE sensor elements (4) were deposited in the free zones (13) in the probe (1). The assembly was left to dry for 24 hours and the functioning of the probe (1) was verified.

It should be noted that, the membranes are prepared using different ionophores in accordance with the analytes/parameters of interest and, if using PVC-based membranes, different plasticisers. Alternatively, the membrane or sensor element can also be prepared using photocurable polymers in its composition instead of PVC, which enables greater automation of the deposition process.

Assay with monitoring probes (measurement of Nitrate and Potassium)—Verification of the functioning of the probes.

Figure 5:
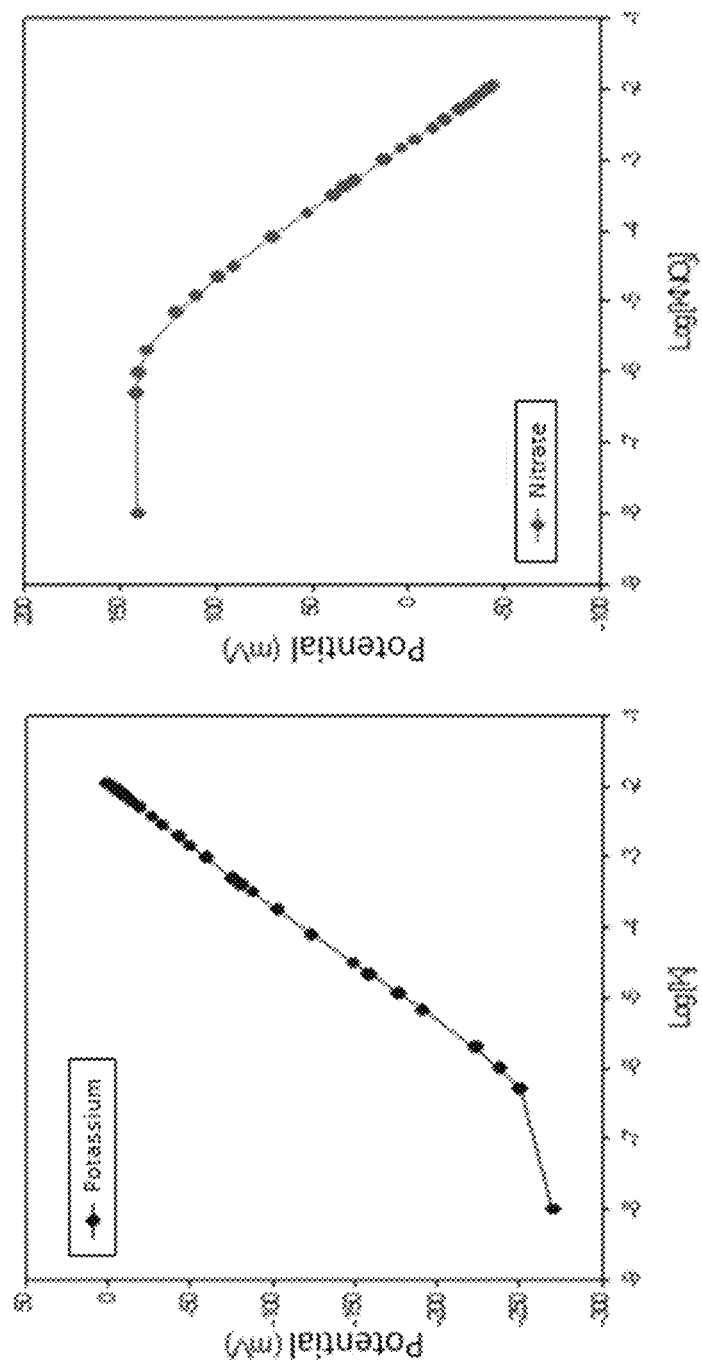
FIG. 5 shows calibration curves obtained in solution with monitoring probes embodied according to the invention.

In order to verify the proper functioning of the probes, it was necessary to obtain their response when submerged in aqueous solutions through their calibration against model solutions with varying concentrations of the species of interest. The calibration curve made it possible to establish the work range with linear response and determine the probe (1) detection limit. FIG. 5 shows the calibration curve for both analytes obtained in a solution with the probe (potassium and nitrate, respectively).

In general, all the probes behaved very similarly to that shown in FIG. 5. As shown in the calibrations, the ISE sensor elements (4) are capable of responding to concentrations of both nitrate and potassium up to the range of $10^{-6}$ M, showing an ample linear response zone. Additionally, after studying the response of both ISE sensor elements (4), a significant influence of potential common interferents, such as chloride and ammonia, in the response of the nitrate and potassium ISE sensor elements (4), respectively, was ruled out.

Figure 6:
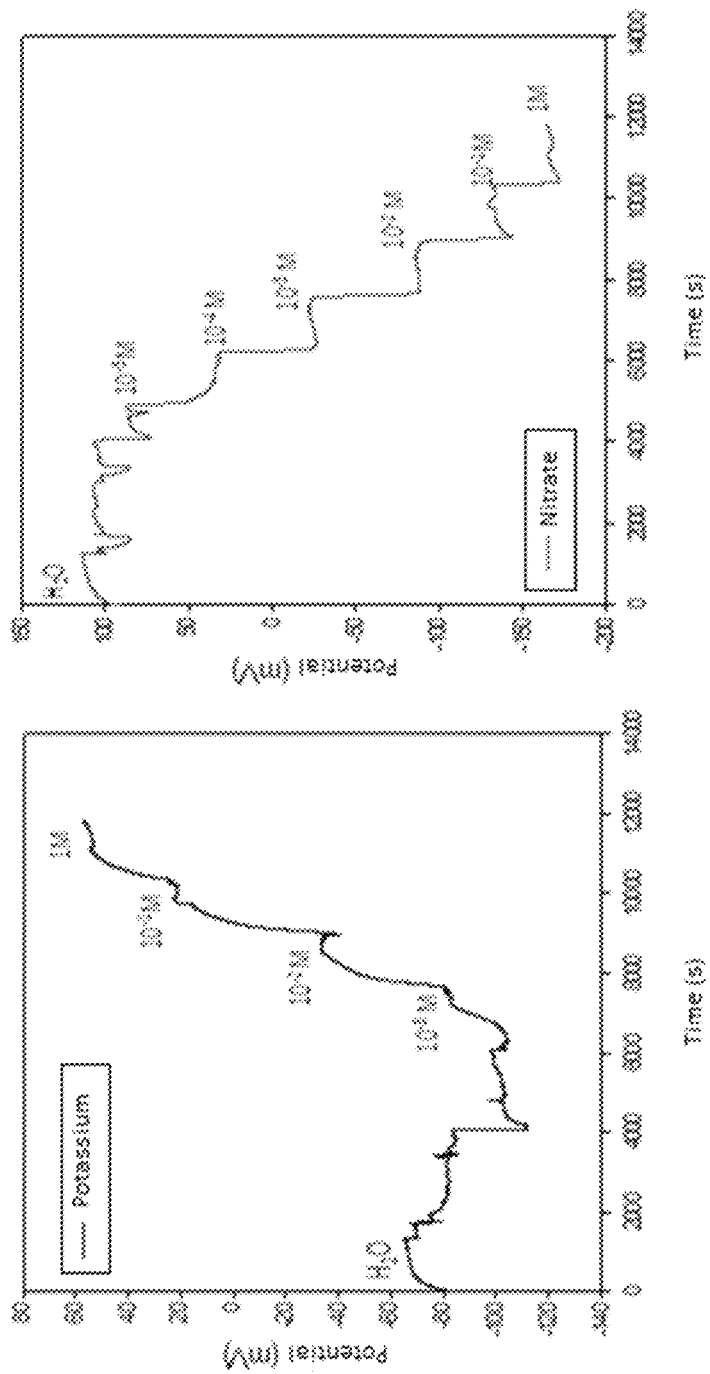
FIG. 6 shows the response of one of the probes embodied according to the invention upon being calibrated in the ground.

Next, in order to verify the operability of the nitrate and potassium monitoring probes directly in the ground, a probe (1) was calibrated in citrus crop soil (ground). To this end, the probe (1) was inserted in fertile soil, sequentially applying solutions with increasing concentrations of $KNO_3$. The graphs of FIG. 6 show the changes of the signal generated in each ISE sensor element (4) of the probe (1) due to the changes in the concentration of the ground solution.

Adaptation of the signal for the acquisition thereof using a datalogger.

The probes (1) were installed in the field and connected to a datalogger (10). This is an electronic device that records real-time data from proprietary or external instruments and sensors connected to the device. In general, they are small, battery-fed, portable and equipped with a microprocessor and internal memory for storing data. These dataloggers are connected to a personal computer and use specific software to activate the datalogger, view them and analyse the data collected.

One of the main benefits of using dataloggers is their capacity to automatically gather information 24 hours a day. Once activated, the dataloggers are normally left unattended to measure and record the information throughout the duration of the monitoring period. This allows a global and accurate view of the conditions subjected to monitoring, such as the temperature, the electrical conductivity of the soil, the relative humidity or, as in our case, the evolution of analytes of interest in the ground itself.

However, the signals generated by the ISE sensors (4) have a very high output impedance, due to which for some commercial dataloggers the signal must previously be conditioned. This electronic conditioning of the signal enables the compatibility and coupling of the work impedances of the devices involved.

In order to overcome this and other limitations, a signal-conditioning electronic board was designed and manufactured. It consists of an instrumentation amplifier (17) for each ISE sensor element (14, 15) that makes it possible to read the floating differential signals generated by them. Since the work range of the ISE sensor elements (14, 15) is between −1 and 1V, it was also necessary to integrate a voltage adder (18) to adapt the signals to the work range of the analogue-to-digital converter at the datalogger inputs (0-2.5 V). In this way, the instrumentation amplifier (17) adds an adjustment potential to signals at the output of the operational amplifiers.

Figure 7:
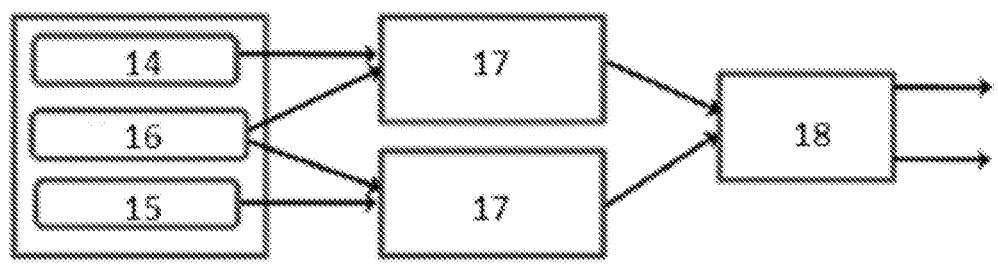
FIG. 7 shows a block diagram of an electronic circuit for adapting and capturing the electrical signals generated by a monitoring probe according to the invention.

FIG. 7 shows a block diagram of the functioning of the electronics developed for the assay with a probe (1) with ISE sensor elements (14, 15) sensitive to nitrate and potassium, respectively. The floating differential signals are obtained from the two ISE sensor elements (14, 15) and the reference signal (16), said signals being amplified in the corresponding instrumentation amplifiers (17), at the output of which the voltage adder is applied (18). The output of the voltage adder is connected to the datalogger (10).

The printed circuit board was designed using surface assembly elements (SAE) for the purpose of reducing the dimensions thereof and selecting the most appropriate elements for minimising the effects of the instrumental noise as much as possible. Thus, the printed circuit board had two connectors, one connected directly to the probe (1) and the second connected directly to the datalogger (10).

The response of the conditioning boards manufactured was electronically evaluated by subjecting them to different levels of input voltage and monitoring their output behaviour. In all cases, both the gradient and the offset coincided with that expected in accordance with the design made.

Since both the probe (1) and the electronic circuit (9) must be installed outdoors, it was necessary to encapsulate this circuit in a watertight box (Standard IP 67) to protect it against ambient factors.

Installation of the monitoring probes in the field.

Figure 8:
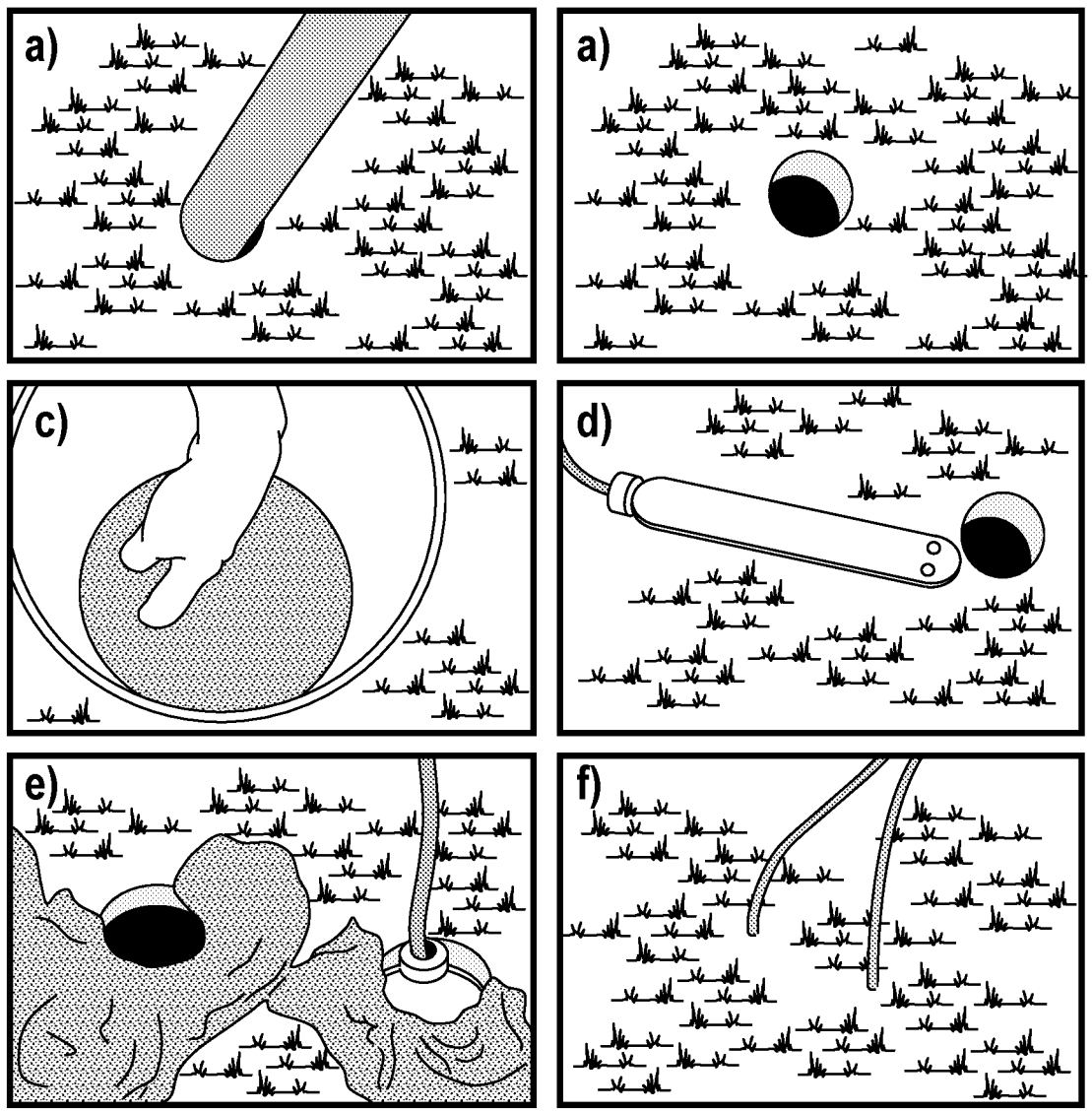
FIG. 8 shows the sequence for installing a probe according to the invention in the field.

In order to install the probes (1) in the field, as shown in FIG. 8, the following stages were followed:

a) A hole was made using a hollow metal tube with a sufficiently large diameter for the probe (1) to fit inside the hole left by the tube.

b) The depth of this hole depends on the profile of the ground in which the parameters of interest are going to be monitored.

c) A fraction of the cultivation ground was taken and sieved, taking a fraction of between 50 and 200 μm, water was added and it was stirred to obtain a viscous sludge.

d) The probe (1) was inserted in the hole.

e) The probe (1) was covered with the sieved sludge, and f) Lastly, it was completely covered with soil from that cultivation area.

In the assay shown in the sequence in FIG. 8, probes were installed at a depth of 15 and 30 cm.

Next, the probe (1) was connected to the electronic circuit (9) for the acquisition and adaptation of the electrical signal from the probe (1) and this, in turn, to the datalogger (10).

Figure 9A:
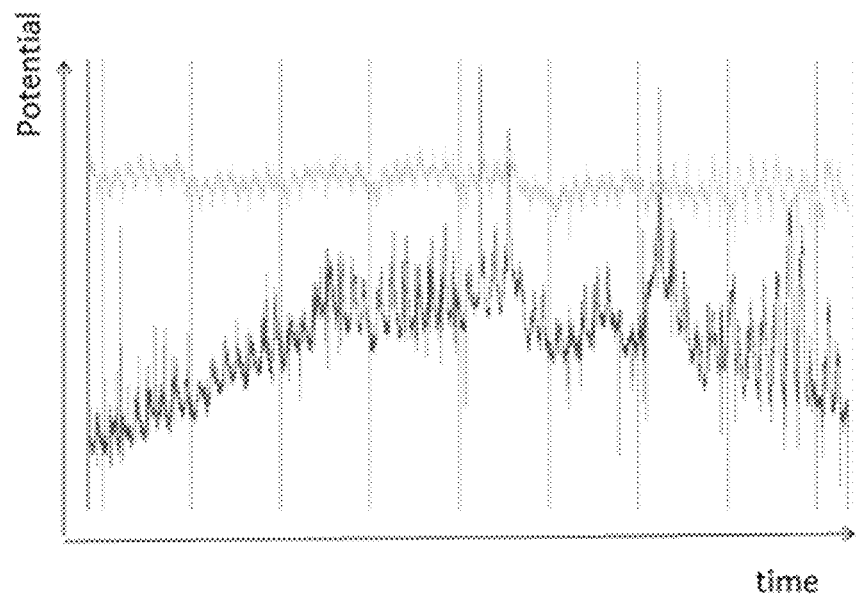
FIGS. 9A-9C show three examples A), B) and C) of graphs obtained by a datalogger connected to a monitoring system according to the invention.
Figure 9B:
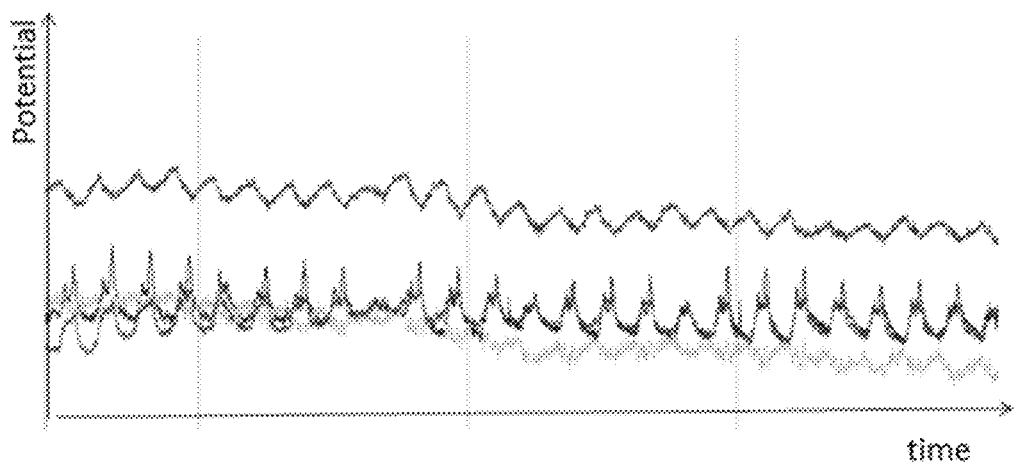
Figure 9C:
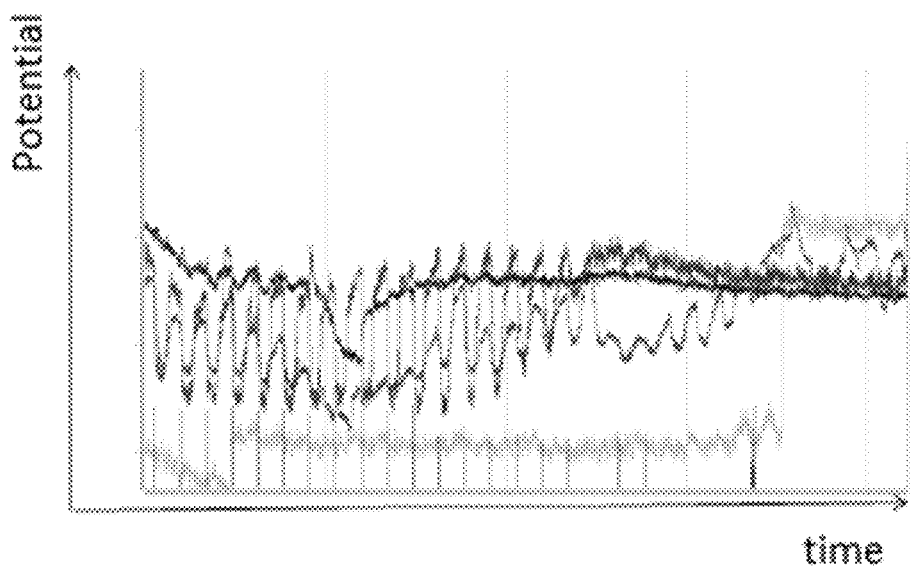

Graphs A), B) and C) of FIG. 9 show examples of graphs obtained using different dataloggers (10). These graphs show the response obtained using nitrate and potassium ISEs in different types of crops and installed at different soil depths.

The invention claimed is:

1. A probe for the continuous monitoring in real time of parameters of interest directly in the ground comprising,
   a substrate with at least two faces,
   at least one conductive material track arranged on at least one of the at least two faces of the substrate, with a zone adapted to act as an electrical contact terminal outside of the probe,
   a conductive region with reference electrode functions arranged on one of the faces of the substrate, with a zone adapted to act as an electrical contact terminal outside of the probe, wherein a material for the at least one conductive track and the conductive region is selected from the group consisting of: metal, non-metallic ink, non-metallic graphite composite, conductive polymers and non-metallic conductive nanomaterials,
   at least one passivating material layer arranged such that it partially covers the at least one conductive material track and leaves at least two free zones thereof, one of said free zones corresponding to the electrical contact terminal of the at least one conductive material track, and
   at least one sensor element sensitive to at least one of the parameters of interest to be monitored in the ground, deposited in at least one of the free zones of the at least one conductive material track, and
   wherein the at least one conductive region occupies one of the faces of the substrate in its entirety.

2. The probe for the continuous monitoring in real time of parameters of interest directly in the ground, according to claim 1, characterised in that,
   the substrate is FR4,
   the at least one conductive region with reference electrode functions has biocidal properties, and
   the at least one sensor element is an ion-selective electrode (ISE).

3. The probe for the continuous monitoring in real time of parameters of interest directly in the ground, according to claim 1, characterised in that when it comprises more than one sensor element they are arranged at the same or different heights, the latter enabling monitoring at different ground depths.

4. The probe for the continuous monitoring in real time of parameters of interest directly in the ground, according to claim 1, characterised in that when it comprises more than one sensor element, each sensor element is sensitive to the same parameter of interest of the ground or to a different parameter of interest of the ground.

5. The probe for the continuous monitoring in real time of parameters of interest directly in the ground, according to claim 1, characterised in that it comprises a receptacle adapted to house a portion of soil of the ground to be monitored, near the at least one sensor element of the monitoring probe.

6. The probe for the continuous monitoring in real time of parameters of interest directly in the ground, according to claim 5, characterised in that the receptacle comprises a porous zone in a substantially lower zone thereof for enabling the evacuation of rain or fertigation water.

7. A system for the continuous monitoring in real time of parameters of interest directly in the ground, characterised in that it comprises,
   at least one probe for the continuous monitoring in real time of the parameters of interest directly in the ground, according to claim 1, and
   at least one electronic circuit connected to the monitoring probe for the acquisition and adaptation of the at least two electrical signals generated by said monitoring probe.

8. The system for the continuous monitoring in real time of parameters of interest directly in the ground, according to claim 7, characterised in that the connection of the at least one electronic circuit to the at least one probe is electrical, through the contact terminals of the probe, or wireless.

9. A system for the continuous monitoring in real time of parameters of interest directly in the ground, according to claim 7, characterised in that it additionally comprises a datalogger or a local data storage system, connected to the electronic circuit for the acquisition and adaptation of an electrical signal generated by the monitoring probe.

10. The system for the continuous monitoring in real time of parameters of interest directly in the ground, according to claim 9, characterised in that the connection of the datalogger to the at least one electronic circuit is cable or wireless.

11. A method for the continuous monitoring in real time of parameters of interest directly in the ground, characterised in that it comprises the following stages:
    a) Providing a monitoring system according to claim 7,
    b) Installing the probe in the ground to be monitored, and
    c) Collecting the data from the ground being monitored by means of the datalogger or a local data storage system.

12. The method for the continuous monitoring in real time of parameters of interest directly in the ground, according to claim 11, characterised in that the installation of the probe in the ground to be monitored comprises the following stages:
    making a hole in the ground sufficiently large to house the probe and with a depth depending on the profile of the ground in which the parameters of interest are to be monitored,
    obtaining a viscous sludge by mixing a sieved fraction of ground to be monitored and water,
    introducing the probe in the hole made in the ground,
    filling the hole with the probe in its interior with the viscous sludge, and
    covering the zone of the hole with the probe filled with the viscous sludge with a portion of soil of the ground itself.

13. The method for the continuous monitoring in real time of parameters of interest directly in the ground, according to claim 12, characterised in that the sieved fraction of the ground to be monitored has a particle size comprised between 15 and 200 microns.

14. A probe for the continuous monitoring in real time of parameters of interest directly in the ground comprising,
    a substrate with at least two faces, at least one conductive material track arranged on at least one of the at least two faces of the substrate, with a zone adapted to act as an electrical contact terminal outside of the probe, a conductive region with reference electrode functions arranged on one of the faces of the substrate, with a zone adapted to act as an electrical contact terminal outside of the probe, wherein a material for the at least one conductive track and the conductive region is selected from the group consisting of: metal, non-metallic ink, non-metallic graphite composite, conductive polymers and non-metallic conductive nanomaterials, at least one passivating material layer arranged such that it partially covers the at least one conductive material track and leaves at least two free zones thereof, one of said free zones corresponding to the electrical contact terminal of the at least one conductive material track, and at least one sensor element sensitive to at least one of the parameters of interest to be monitored in the ground, deposited in at least one of the free zones of the at least one conductive material track, and wherein the substrate is FR4, the at least one conductive region with reference electrode functions has biocidal properties, and the at least one sensor element is an ion-selective electrode (ISE).

15. A probe for the continuous monitoring in real time of parameters of interest directly in the ground comprising, a substrate with at least two faces, at least one conductive material track arranged on at least one of the at least two faces of the substrate, with a zone adapted to act as an electrical contact terminal outside of the probe, a conductive region with reference electrode functions arranged on one of the faces of the substrate, with a zone adapted to act as an electrical contact terminal outside of the probe, wherein a material for the at least one conductive track and the conductive region is selected from the group consisting of: metal, non-metallic ink, non-metallic graphite composite, conductive polymers and non-metallic conductive nanomaterials, at least one passivating material layer arranged such that it partially covers the at least one conductive material track and leaves at least two free zones thereof, one of said free zones corresponding to the electrical contact terminal of the at least one conductive material track, at least one sensor element sensitive to at least one of the parameters of interest to be monitored in the ground, deposited in at least one of the free zones of the at least one conductive material track, and a receptacle adapted to house a portion of soil of the ground to be monitored, near the at least one sensor element of the monitoring probe.

\* \* \* \* \*